(12) United States Patent
Verhaak et al.

(10) Patent No.: US 9,260,366 B2
(45) Date of Patent: Feb. 16, 2016

(54) PROCESS FOR THE PRODUCTION OF ETHYLENE OXIDE

(71) Applicant: SHELL OIL COMPANY, Houston, TX (US)

(72) Inventors: Michael Johannes Franciscus Maria Verhaak, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/717,189

(22) Filed: May 20, 2015

(65) Prior Publication Data

US 2015/0251979 A1 Sep. 10, 2015

Related U.S. Application Data

(63) Continuation of application No. 13/980,927, filed as application No. PCT/EP2012/050988 on Jan. 23, 2012, now Pat. No. 9,067,901.

(30) Foreign Application Priority Data

Jan. 24, 2011 (EP) .................................... 11151793

(51) Int. Cl.
| | |
|---|---|
| C07C 1/00 | (2006.01) |
| C07C 29/10 | (2006.01) |
| C07D 301/10 | (2006.01) |
| C07C 29/132 | (2006.01) |
| C07C 1/20 | (2006.01) |
| C07D 301/03 | (2006.01) |

(52) U.S. Cl.
CPC ............... C07C 29/106 (2013.01); C07C 1/20 (2013.01); C07C 29/132 (2013.01); C07D 301/03 (2013.01); C07D 301/10 (2013.01)

(58) Field of Classification Search
CPC .... C07C 29/095; C07C 31/202; C07C 11/34; C07C 9/06; C07C 1/20
USPC .......................................... 568/864; 585/323
See application file for complete search history.

(56) References Cited

U.S. PATENT DOCUMENTS

| | | | |
|---|---|---|---|
| 4,990,632 A | 2/1991 | Ramachandran et al. | |
| 5,929,258 A | 7/1999 | Hayashi et al. | |
| 5,990,369 A | 11/1999 | Barger et al. | |
| 6,518,476 B1 | 2/2003 | Culp et al. | |
| 7,091,377 B2 | 8/2006 | Borgmeier et al. | |
| 7,132,580 B1 | 11/2006 | Senetar | |
| 7,504,545 B2 | 3/2009 | Boele et al. | |
| 2004/0224841 A1 | 11/2004 | Matusz et al. | |
| 2004/0225138 A1 | 11/2004 | McAllister et al. | |
| 2004/0247393 A1 | 12/2004 | Hess et al. | |
| 2007/0155999 A1 | 7/2007 | Pujado et al. | |
| 2007/0203380 A1 | 8/2007 | Vora et al. | |
| 2008/0139853 A1 | 6/2008 | Boele et al. | |
| 2008/0182999 A1 | 7/2008 | Rekers et al. | |
| 2009/0234144 A1 | 9/2009 | Bos et al. | |
| 2009/0259077 A1* | 10/2009 | Van Kruchten | C07C 29/095 568/864 |
| 2009/0281345 A1 | 11/2009 | Matusz | |
| 2010/0256432 A1 | 10/2010 | Arnold et al. | |
| 2011/0009653 A1 | 1/2011 | Mazanec et al. | |
| 2011/0137095 A1* | 6/2011 | Chewter | C01B 3/24 585/323 |

FOREIGN PATENT DOCUMENTS

| | | |
|---|---|---|
| CN | 1041591 | 4/1990 |
| CN | 1215041 | 4/1999 |
| CN | 1237481 | 12/1999 |
| CN | 1269341 | 10/2000 |
| CN | 1463960 | 12/2003 |
| CN | 101362669 | 2/2009 |
| EP | 0850936 | 7/1998 |
| GB | 1213483 | 12/1970 |
| GB | 1314613 | 4/1973 |
| WO | 0236532 | 1/2002 |
| WO | 03064035 | 4/2003 |
| WO | 2006020083 | 2/2006 |
| WO | 2007135052 | 11/2007 |
| WO | 2009065848 | 5/2009 |
| WO | 2009065855 | 5/2009 |
| WO | 2009065870 | 5/2009 |
| WO | 2009065875 | 5/2009 |
| WO | 2009065877 | 5/2009 |
| WO | 2010096909 | 9/2010 |
| WO | 2011057976 | 5/2011 |
| WO | 2011057980 | 5/2011 |

OTHER PUBLICATIONS

Kniel L. et al., "Ethylene, Keystone to the Petrochemical Industry", Marcel Dekker, Inc., New York, 1980, Chapters 6&7, pp. 62-108.
Zimmerman, H. et al., "Ethylene", Linde Engineering Division, Wiley-VCH Verlag GmbH & Co. KGaA, Weinheim, 2009, Germany, pp. 1-66.
Kobe, J.M. et al; "Epoxidation-INDUSTRIAL"; Encyclopedia of Catalysis; 2003, vol. 3; pp. 246-248.
Cheng, Huiming et al.: Adv. i Process Res. of Methanol to Light Olefins, Guadong Chem Ind., vol. 37, No. 4, Apr. 25, 2010, pp. 27-33.
Dai, Bing-xin, et al.: Technology Development of Coal-based Methanol-to-Olefins in China, Heinan Chem Ind., vol. 27, No. 4, 2010, pp. 25-28.
Li, Lixen et al.: Progress of Sep. Tech. For Methanol to Olefins, Chem Ind and Eng Progress, vol. 27, No. 9 Sep. 5, 2008. pp. 1332-1335.
Tech. Dept of Tanjin Uni, Technical & Res.sec,: Basic organic synthesis tech. Chem Ind Press, 1959-04, vol. 30, No. 10, Oct. 31, 2010, pp. 33-36.
Xing, Aihua et al.: Recent adv. in typical tech. For methanol conversion to olefins, Mod. Che Ind., vol. 30, No. 10, Oct. 31, 2010, pp. 18-25, Oct. 2010.

* cited by examiner

Primary Examiner — Jafar Parsa

(57) ABSTRACT

The invention relates to a process for the production of ethylene oxide, comprising the steps of: producing ethylene by converting a stream comprising an oxygenate into a stream comprising ethylene and ethane; producing ethylene oxide by subjecting ethylene and ethane from the stream comprising ethylene and ethane to oxidation conditions resulting in a stream comprising ethylene oxide, unconverted ethylene and ethane; and recovering ethylene oxide from the stream comprising ethylene oxide, unconverted ethylene and ethane.

11 Claims, 2 Drawing Sheets

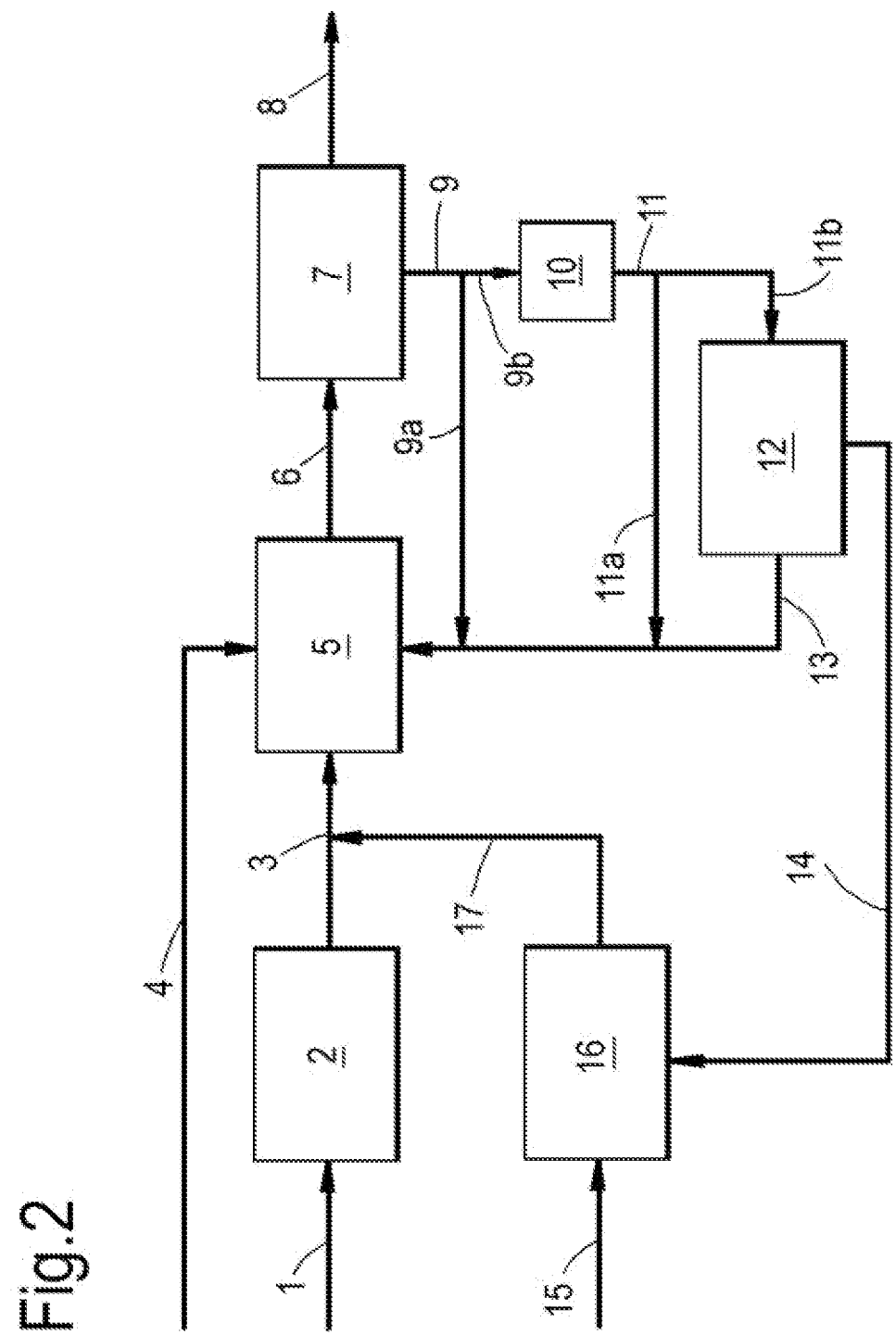

PROCESS FOR THE PRODUCTION OF ETHYLENE OXIDE

The present application is a continuation of U.S. application Ser. No. 13/980,927 filed Sep. 30, 2013, which is the National Stage (§371) of International Application PCT/EP2012/050988, filed Jan. 23, 2012, and which claims the benefit of European Patent Application No. 11151793.4 filed Jan. 24, 2011, all of which are incorporated herein by reference.

FIELD OF THE INVENTION

The present invention relates to a process for the production of ethylene oxide.

In recent years, increasing attention has been given to the exploration and utilisation of natural gas resources around the globe. A disadvantage of natural gas with respect to oil is the difficulty to transport large volumes of natural gas from the source to the market. One way of efficiently transporting natural gas is by liquefying the natural gas and to transport the liquefied natural gas (LNG).

Another way is to convert the methane in the natural gas to liquid derivatives, which can also be transported at relative ease. One liquid derivative of interest may for instance be monoethylene glycol (MEG). MEG is a liquid at room temperature and can therefore be suitably transported. MEG is produced by reacting ethylene oxide with water.

In WO200236532, a process for preparing ethylene oxide from methane is described. In the process of WO200236532, methane is converted to methanol, via syngas, and the methanol is subsequently converted to a product stream comprising ethylene via a Methanol-to-Olefins (MTO) process. The product steam comprises, in addition to ethylene, also paraffinic compounds, such as ethane. The production of ethane as a by-product in said ethylene production process is for example also disclosed in U.S. Pat. No. 5,990,369 and U.S. Pat. No. 7,132,580.

These paraffinic compounds are separated from the ethylene prior to sending the ethylene to the ethylene oxidation unit. The ethane is typically sent as fuel to a furnace. However, the separation of ethane from ethylene leads to loss of ethylene as part of the ethylene will be removed together with the ethane, in particular if a high purity of the ethylene is sought. Consequently, ethylene oxide and thus MEG yields of the process, based on the methane provided, are reduced.

SUMMARY OF THE INVENTION

An object of the present invention is to provide a process for the production of ethylene oxide by producing ethylene by conversion of an oxygenate, such as methanol, and producing ethylene oxide by oxidation of said ethylene, which process does not have the above drawback.

Surprisingly, it was found that the above drawback is avoided by means of an integrated process wherein ethylene is produced by converting a stream comprising an oxygenate into a stream comprising ethylene and ethane, wherein ethylene and ethane from the latter stream are subjected to oxidation conditions resulting in the desired ethylene oxide.

Accordingly, the present invention relates to a process for the production of monoethylene glycol, comprising the steps of:

producing ethylene by converting a stream comprising an oxygenate into a first product stream comprising ethylene and ethane through an oxygenate-to-olefins process;

producing ethylene oxide by subjecting ethylene and ethane from the first product stream comprising ethylene and ethane to oxidation conditions resulting in a second product stream comprising ethylene oxide, unconverted ethylene and ethane;

recovering ethylene oxide from the second product stream comprising ethylene oxide, unconverted ethylene and ethane; and converting the ethylene oxide to monoethylene glycol through an hydrolysis reaction.

BRIEF DESCRIPTION OF THE DRAWINGS

FIG. 2 is a schematic illustration of a second preferred embodiment of the invention.

DETAILED DESCRIPTION

Figure 1:
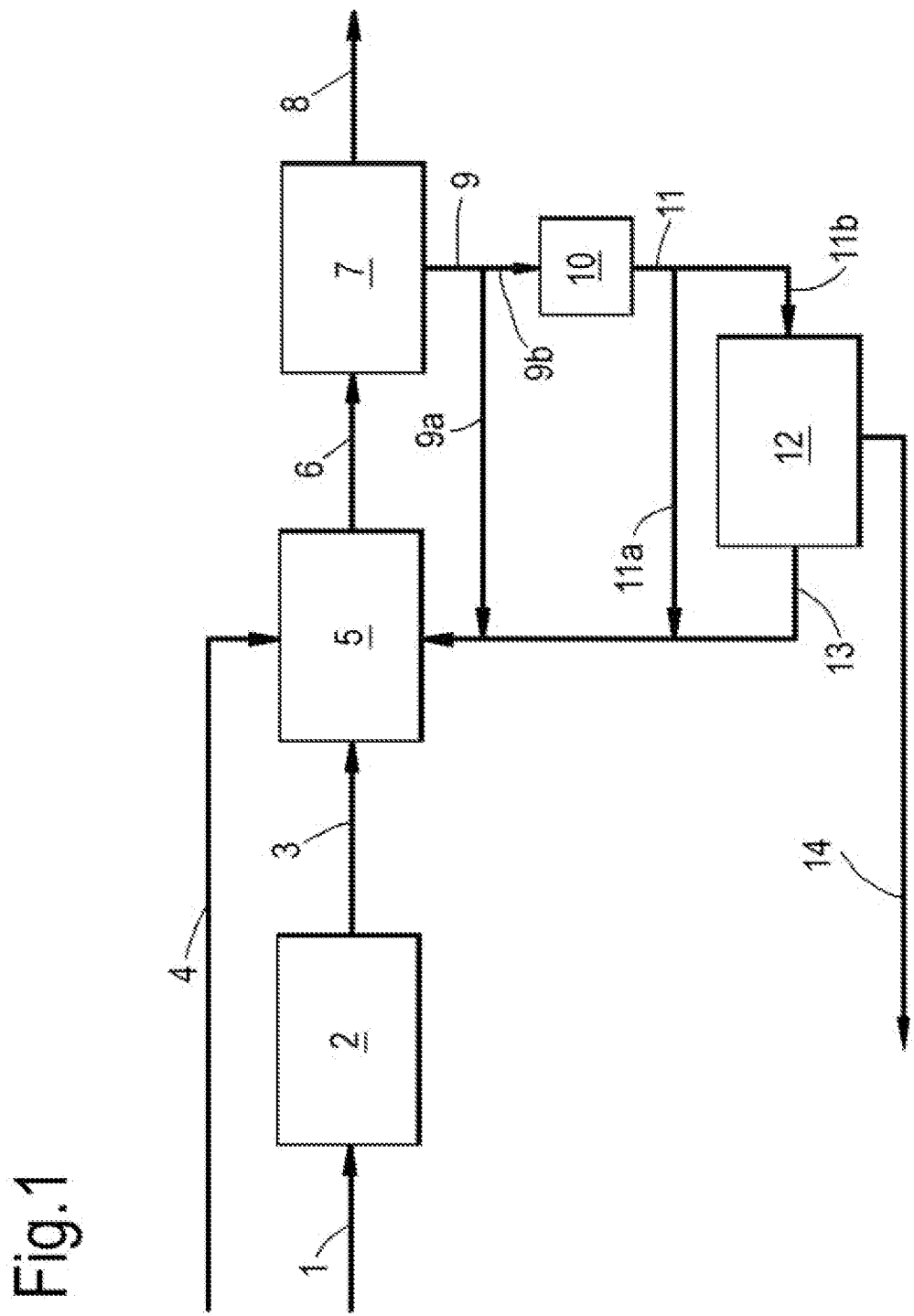
FIG. 1 is a schematic illustration of a preferred embodiment of the invention.

An advantage of the present invention is that no ethane has to be separated from the ethylene containing product stream that results from the ethylene production step. This results in a much simpler overall process using less separation processes and equipment, as compared to for example the process of FIG. 1 of above-mentioned U.S. Pat. No. 5,990,369 as explained at column 10, line 26 and further of said U.S. Pat. No. 5,990,369 and said WO200236532.

In addition, the non-separated ethane advantageously functions as a ballast gas in the next ethylene oxidation step so that no or substantially less additional ballast gas needs to be added. Because an oxidizing agent is required, it is important to control the safe operability of the reaction mixture, which can generally be done by adding a ballast gas. Common ballast gases in the production of ethylene oxide by oxidation of ethylene, are nitrogen and methane.

Still further, separation of the stream comprising ethylene and ethane resulting from the ethylene production step of the present process is advantageously automatically, and at least partially, effected in the ethylene oxide production step wherein the ethylene is consumed and converted into ethylene oxide which can be separated more easily from the non-consumed ethane.

All these and other advantages result in a substantial reduction of expenditure, for example savings on costs for compression, refrigeration, etc. needed for separating ethane from the ethylene. These and other advantages are further described below.

GB1314613 discloses the use of ethane as a ballast gas in the production of ethylene oxide from ethylene. However, the integrated process of the present invention is not disclosed and is neither suggested in GB1314613.

The ethylene oxidation step in the present process results in a stream comprising ethylene oxide, unconverted ethylene and ethane. The ethylene oxide can be recovered easily from such stream by means of methods known to the skilled person. That is to say, ethylene oxide may be separated from said stream comprising ethylene oxide, unconverted ethylene and ethane resulting in a stream comprising unconverted ethylene and ethane. The unconverted ethylene and the ethane from the latter stream may be recycled within the present process and advantageously be converted and re-used, respectively, after such recycle. After ethylene oxide is separated from said stream comprising ethylene oxide, unconverted ethylene and ethane and before such recycle of the remaining unconverted ethylene and ethane, any carbon dioxide is removed. That is to say, either part or all carbon dioxide is removed. Said carbon dioxide may be produced in the ethylene oxide production step. Ways of removing carbon dioxide, such as a caustic wash, are known to the skilled person. The removed carbon dioxide may be used to produce methanol, from hydrogen and said carbon dioxide and optionally carbon monoxide, which methanol can then be used as a feedstock for the ethylene production step comprising oxygenate conversion of the present invention.

Unconverted ethylene, and optionally ethane, from the stream comprising ethylene oxide, unconverted ethylene and ethane resulting from the step of producing ethylene oxide may be recycled to that step of producing ethylene oxide. That is to say, either part or all unconverted ethylene, and optionally ethane, is recycled in such way. The recycled unconverted ethylene is then advantageously converted as yet in that ethylene oxidation step. Further, the recycled ethane is then advantageously re-used as a ballast gas in that ethylene oxidation step. In this embodiment, preferably, a stream comprising unconverted ethylene and ethane is separated from the stream comprising ethylene oxide, unconverted ethylene and ethane resulting from the step of producing ethylene oxide, and is then recycled to the step of producing ethylene oxide. Such recycle has both said advantages in that conversion of unconverted ethylene into ethylene oxide is effected as yet, whereas re-use of ethane as a ballast gas is also effected at the same time.

Where in the present specification reference is made to recycling to the "step of producing ethylene oxide", "ethylene oxide production step" or "ethylene oxidation step", such step not only covers the step(s) of production of the desired product in question but also the step(s) of work-up of the product stream in question.

An embodiment of the present invention is shown in FIG. 1.

In the flow scheme of FIG. 1, stream 1 comprising a feed containing an oxygenate is fed to ethylene production unit 2. Stream 3 comprising ethylene and ethane and stream 4 comprising an oxidizing agent, such as high-purity oxygen or air, are fed to ethylene oxide production unit 5. Stream 6 comprising ethylene oxide, unconverted ethylene, ethane and carbon dioxide is sent to ethylene oxide separation unit 7. Ethylene oxide is recovered via stream 8. Further, stream 9 comprising unconverted ethylene, ethane and carbon dioxide is split into two substreams 9a and 9b. Substream 9a is recycled to ethylene oxide production unit 5. Substream 9b is fed to carbon dioxide removal unit 10. Stream 11 comprising unconverted ethylene and ethane is split into two substreams 11a and 11b. Substream 11a is recycled to ethylene oxide production unit 5. Substream 11b is fed to ethylene/ethane separation unit 12. Stream 13 comprising unconverted ethylene is recycled to ethylene oxide production unit 5. Stream 14 comprising ethane may be discarded. Further, a third stream may be separated in ethylene/ethane separation unit 12, namely a top bleed stream comprising uncondensable components, such as oxygen and/or argon (said third stream not shown in FIG. 1). Still further, stream 3 may be subjected to hydrotreatment in a hydrotreater unit before entering ethylene oxide production unit 5 (said hydrotreater unit not shown in FIG. 1) to convert any acetylene present. In general, in the conversion of an oxygenate, such as methanol, into ethylene hydrogen may be produced as a by-product. Separating hydrogen from the stream comprising ethylene and ethane is not essential in terms of obtaining the advantages of the present invention as described herein. It is even preferred that hydrogen, if any, is not separated from the latter stream. In this way, at least part of the hydrogen may be used to convert at least part of the acetylene.

In the ethylene oxide production step of the present process, ethylene oxide is produced by subjecting ethylene and ethane from the stream comprising ethylene and ethane, originating from the ethylene production step, to oxidation conditions resulting in a stream comprising ethylene oxide, unconverted ethylene and ethane.

An advantage of the present process is that the product stream resulting from the ethylene production step also comprises ethane, in addition to ethylene that is to be oxidized in the next step. Ethane is a suitable ballast gas in the oxidation of ethylene. As discussed above, normally nitrogen or methane is added as a ballast gas in the oxidation of ethylene. Now that in the present invention, ethane present in the ethylene containing product stream resulting from the ethylene production step functions as a ballast gas in the ethylene oxide production step, no or substantially less of a separate ballast gas, such as nitrogen or methane, has to be added. This results in a much simpler and more efficient ethylene oxidation process.

In the ethylene oxide production step of the present process, ethylene and ethane from the stream comprising ethylene and ethane are contacted with an oxidizing agent. The oxidizing agent may be high-purity oxygen or air, but is preferably high-purity oxygen which may have a purity greater than 90%, preferably greater than 95%, more preferably greater than 99%, and most preferably greater than 99.9%. Typical reaction pressures are 1-40 bar, suitably 10-30 bar, and typical reaction temperatures are 100-400° C., suitably 200-300° C.

Further, the amounts of ethylene and ethane, respectively, as fed to the ethylene oxide production step of the present process, may be of from 10 to 90 wt. %, suitably of from 20 to 80 wt. % of ethylene, and 90 to 10 wt. %, suitably of from 80 to 20 wt. % of ethane, respectively, all said amounts based on the total amount of the stream or the streams comprising ethylene and/or ethane as fed to said ethylene oxide production step.

The minimum amount of ethylene as referred to above may be 1 wt. %, 5 wt. %, wt. %, 20 wt. %, 25 wt. %, 30 wt. % or 35 wt. %. The maximum amount of ethylene as referred to above may be 99 wt. %, 95 wt. %, 90 wt. %, 80 wt. %, 70 wt. %, 60 wt. %, 55 wt. %, 50 wt. % or 45 wt. %. The minimum amount of ethane as referred to above may be 1 wt. %, 5 wt. %, 10 wt. %, 20 wt. %, 25 wt. %, 30 wt. % or 35 wt. %. The maximum amount of ethane as referred to above may be 99 wt. %, 95 wt. %, 90 wt. %, 80 wt. %, 70 wt. %, 60 wt. %, 55 wt. %, 50 wt. % or 45 wt. %.

In case the ethylene production step comprising oxygenate conversion does not result in sufficient ethane for use as ballast gas in the ethylene oxide production step, additional ethane may be added to the ethylene oxide production step. The source of the ethane may be any source. For example, additional ethane may originate from steam cracking a hydrocarbon stream as further discussed below. Additional ethane may be added in such amount that the amount of ethane as referred to above falls within any of the above-mentioned ranges for ethane.

Further, it is preferred that in the ethylene oxide production step of the present process, the ethylene and ethane are contacted with a catalyst, preferably a silver containing catalyst. A typical reactor for the ethylene oxide production step consists of an assembly of tubes that are packed with catalyst. A coolant may surround the reactor tubes, removing the reaction heat and permitting temperature control.

In case a silver containing catalyst is used in the ethylene oxide production step of the present process, the silver in the silver containing catalyst is preferably in the form of silver oxide. Preferred is a catalyst comprising particles wherein silver is deposited on a carrier. Suitable carrier materials include refractory materials, such as alumina, magnesia, zirconia, silica and mixtures thereof. The catalyst may also contain a promoter component, e.g. rhenium, tungsten, molybdenum, chromium, nitrate- or nitrite-forming compounds and combinations thereof. Preferably, the catalyst is a pelletized catalyst, for example in the form of a fixed catalyst bed, or a powdered catalyst, for example in the form of a fluidized catalyst bed.

The nature of the ethylene oxidation catalyst, if any, is not essential in terms of obtaining the advantages of the present invention as described herein. The amount of the ethylene oxidation catalyst is neither essential. If a catalyst is used, preferably a catalytically effective amount of the catalyst is used, that is to say an amount sufficient to promote the ethylene oxidation reaction. Although a specific quantity of catalyst is not critical to the invention, preference may be expressed for use of the catalyst in such an amount that the gas hourly space velocity (GHSV) is of from 100 to 50,000 $hr^{-1}$, suitably of from 500 to 20,000 $hr^{-1}$, more suitably of from 1,000 to 10,000 $hr^{-1}$, most suitably of from 2,000 to 4,000 $hr^{-1}$.

In the present specification, "GHSV" or gas hourly space velocity is the unit volume of gas at normal temperature and pressure (0° C., 1 atmosphere, i.e. 101.3 kPa) passing over one unit volume of catalyst per hour.

A moderator, for example a chlorohydrocarbon such as monochloroethane (ethyl chloride), vinyl chloride or dichloroethane, may be supplied for catalyst performance control in the ethylene oxide production step of the present process. Most suitably, ethyl chloride is used.

Moderators that can be suitably used in the ethylene oxide production step of the present process are also disclosed in above-mentioned GB1314613, the disclosure of which is herein incorporated by reference. GB1314613 discloses the use of an inhibitor (that is to say, a moderator), selected from ethylene dichloride, vinyl chloride, dichlorobenzene, monochlorobenzene, dichloromethane, and chlorinated phenyls, chlorinated biphenyls and chlorinated polyphenyls, in the production of ethylene oxide from ethylene.

The nature of the moderator, if any, is not essential in terms of obtaining the advantages of the present invention as described herein. The amount of the moderator is neither essential. The amount of such moderator in the reaction mixture may range from 1 part per million by volume (ppmv) to 2 vol. %, suitably 1 to 1,000 ppmv. The minimum amount of moderator in the reaction mixture may be 0.1 ppmv, 0.2 ppmv, 0.5 ppmv, 1 ppmv, 2 ppmv, 5 ppmv, 10 ppmv or 50 ppmv. The maximum amount of moderator in the reaction mixture may be 2 vol. %, 1 vol. %, 1,000 ppmv, 800 ppmv or 700 ppmv.

A suitable range for the amount of moderator that can be used in the ethylene oxide production step of the present process is also disclosed in above-mentioned GB1314613 in relation to the above-mentioned group of specific inhibitors (that is to say, moderators) as disclosed in said GB1314613, the disclosure of which is herein incorporated by reference.

Examples of ethylene oxidation processes, including catalysts and other process conditions, are for example disclosed in US20090281345 and above-mentioned GB1314613, the disclosures of which are herein incorporated by reference. All of these ethylene oxidation processes are suitable for the ethylene oxidation step of the present invention.

The process of the present invention comprises a step of producing ethylene which step comprises converting a stream comprising an oxygenate. In this step, the oxygenate in the stream comprising the oxygenate is converted to an olefin (said ethylene) by an Oxygenate-to-Olefins (OTO) process.

Within the present specification, an "oxygenate" means a compound which contains at least one oxygen-bonded alkyl group. The alkyl group preferably is a C1-C4 alkyl group, more preferably a C1-C2 alkyl group and most preferably a C1 alkyl group. The oxygenate may comprise one or more of such oxygen-bonded C1-C4 alkyl groups. Preferably, the oxygenate comprises one or two oxygen-bonded C1-C4 alkyl groups. More preferably an oxygenate is used having at least one C1 or C2 alkyl group, still more preferably at least one C1 alkyl group.

Preferably the oxygenate is chosen from the group of alcohols and dialkyl ethers consisting of dimethylether, diethylether, methylethylether, methanol, ethanol and isopropanol, and mixtures thereof. Most preferably the oxygenate is methanol or dimethylether, or a mixture thereof.

In the process of the present invention, a stream comprising an oxygenate is converted into a stream comprising ethylene and ethane. The ethane from the stream resulting from said step of the present process is produced as a by-product by conversion of the desired ethylene product.

Examples of oxygenate-to-olefins processes, including catalysts and other process conditions, are for example disclosed in US20060020155 (in particular in paragraphs [0116] to [0135] thereof), US20070203380, US20070155999, US20090187058, US20100298619, US20100268007, U.S. Pat. No. 8,269,056, U.S. Pat. No. 8,884,090 and US20100268009, the disclosures of which are herein incorporated by reference. All of these oxygenate-to-olefins processes are suitable for the ethylene production step of the present invention said step comprising oxygenate conversion.

In said ethylene production step of the present invention, the stream comprising an oxygenate is contacted with a catalyst.

Catalysts suitable for converting the oxygenate comprise molecular sieve. Such molecular sieve-comprising catalysts typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

For example, catalysts as described in above-mentioned US20060020155 are suitable for converting said oxygenate comprising stream. Preferably, such catalyst is a molecular sieve catalyst.

Suitable molecular sieves are silicoaluminophosphates (SAPO), such as SAPO-17, -18, 34, -35, -44, but also SAPO-5, -8, -11, -20, -31, -36, 37, -40, -41, -42, -47 and -56; aluminophosphates (AlPO) and metal substituted (silico)aluminophosphates (MeAlPO), wherein the Me in MeAlPO refers to a substituted metal atom, including metal selected from one of Group IA, IIA, IB, IIIB, IVB, VB, VIB, VIIB, VIIIB and Lanthanides of the Periodic Table of Elements. Preferably Me is selected from one of the group consisting of Co, Cr, Cu, Fe, Ga, Ge, Mg, Mn, Ni, Sn, Ti, Zn and Zr.

Alternatively, the conversion of the oxygenate may be accomplished by the use of an aluminosilicate-comprising catalyst, in particular a zeolite-comprising catalyst. Suitable catalysts include those containing a zeolite of the ZSM group, in particular of the MFI type, such as ZSM-5, the MTT type, such as ZSM-23, the TON type, such as ZSM-22, the MEL type, such as ZSM-11, and the FER type. Other suitable zeolites are for example zeolites of the STF-type, such as SSZ-35, the SFF type, such as SSZ-44 and the EU-2 type, such as ZSM-48.

Aluminosilicate-comprising catalyst, and in particular zeolite-comprising catalyst are preferred when an olefinic co-feed is fed to the oxygenate conversion zone together with oxygenate, for increased production of ethylene and propylene.

Preferred catalysts comprise a more-dimensional zeolite, in particular of the MEI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably, the channels in at least one of the directions are 10-membered ring channels. A preferred MFI-type zeolite has a silica-to-alumina ratio, SAR, of at least 60, preferably at least 80. More preferred MFI-type zeolite has a silica-to-alumina ratio, SAR, in the range of 60 to 150, preferably in the range of 80 to 100.

In one embodiment the catalysts include catalysts comprising one or more zeolites having one-dimensional 10-membered ring channels, i.e. one-dimensional 10-membered ring channels, which are not intersected by other channels. Preferred examples are zeolites of the MTT and/or TON type. In a particularly example of this embodiment the catalyst comprises in addition to one or more more-dimensional zeolite, in particular of the MFI type, more in particular ZSM-5, or of the MEL type, such as zeolite ZSM-11, an one-dimensional zeolites having 10-membered ring channels, such as of the MTT and/or TON type.

The catalyst may further comprise phosphorus as such or in a compound, i.e. phosphorus other than any phosphorus included in the framework of the molecular sieve. It is preferred that a MEL or MFI-type zeolite comprising catalyst additionally comprises phosphorus. The phosphorus may be introduced by pre-treating the MEL or MR-type zeolites prior to formulating the catalyst and/or by post-treating the formulated catalyst comprising the MEL or MFI-type zeolites. Preferably, the catalyst comprising MEL or MFI-type zeolites comprises phosphorus as such, i.e. in elemental form, or in a compound in an elemental amount of from 0.05 to 10 wt. % based on the weight of the formulated catalyst. A particularly preferred catalyst comprises phosphorus and MEL or MFI-type zeolite having SAR of in the range of from 60 to 150, more preferably of from 80 to 100. An even more particularly preferred catalyst comprises phosphorus and ZSM-5 having SAR of in the range of from 60 to 150, more preferably of from 80 to 100.

Preferably, the catalyst is a pelletized catalyst, for example in the form of a fixed catalyst bed, or a powdered catalyst, for example in the form of a fluidized catalyst bed.

The nature of the oxygenate-to-olefins catalyst is not essential in terms of obtaining the advantages of the present invention as described herein.

The amount of the oxygenate-to-olefins catalyst is neither essential. Preferably a catalytically effective amount of the catalyst is used, that is to say an amount sufficient to promote the oxygenate-to-olefins conversion. Although a specific quantity of catalyst is not critical to the invention, preference may be expressed for use of the catalyst in such an amount that the gas hourly space velocity (GHSV) is of from 50 to 50,000 $hr^{-1}$, more preferably of from 100 to 20,000 $hr^{-1}$, most preferably of from 150 to 5,000 $hr^{-1}$.

In said oxygenate-to-olefins process that is part of the process of the present invention, typical reaction pressures are 1 mbar to 50 bar, suitably 1-15 bar, and typical reaction temperatures are 200-1000° C., suitably 250-750° C.

Preferably, the stream comprising an oxygenate additionally comprises at least a C4 and/or a C5 olefin or, alternatively, a stream comprising at least a C4 and/or a C5 olefin is co-fed to the step of producing ethylene together with the stream comprising an oxygenate.

In general, the product stream resulting from the ethylene production step comprising oxygenate conversion in the process of the present invention comprises water in addition to ethylene and ethane. Water may easily be separated from said product stream, for example by cooling down the product stream from the reaction temperature to a lower temperature, for example room temperature, so that the water condenses and can then be separated from the product stream.

After separating water, as described above, the resulting stream comprising ethylene and ethane, from which the water is separated, may be further conventionally washed with a caustic solution, in order to neutralize and remove any acid gases present in the latter stream, and then dried.

In general, in the conversion of an oxygenate, such as methanol, into ethylene, methane may be produced as a by-product. Separating any methane from the stream comprising ethylene and ethane is not essential in terms of obtaining the advantages of the present invention as described herein. It is even preferred that methane, if any, is not separated from the latter stream. In this way, methane may function as a ballast gas, in combination with ethane, in the ethylene oxidation step. This is advantageous first of all in that the methane does not have be separated, which is cumbersome, and secondly in that in a case where additional ballast gas needs to be added to the ethylene oxide production step, this may no longer be needed as the mixture of methane and ethane may provide a sufficient amount of ballast gas for the ethylene oxide production step.

The process of the present invention comprises a step of producing ethylene which comprises converting a stream comprising an oxygenate into a stream comprising ethylene and ethane as discussed above. In addition, the process of the present invention may comprise one or more other steps of producing ethylene. Such other ethylene production process(es) is (are) to be carried out in a reactor or reactors different from the reactor wherein a stream comprising an oxygenate is converted. An example of such other ethylene production process is steam cracking hydrocarbon streams, such as an ethane stream, a naphtha stream, a gasoil stream or a hydrowax stream, into ethylene. It is envisaged that ethylene and ethane originating from converting a stream comprising an oxygenate into a stream comprising ethylene and ethane as discussed above, and ethylene and ethane originating from another process or other processes of preparing ethylene, such as said steam cracking, may be fed, either in combination or separately, to the step of oxidation of ethylene into ethylene oxide. Such integrated process is discussed below inter alia with reference to steam cracking of an ethane stream.

A preferred embodiment of the present process for the production of monoethylene glycol, comprising the steps of:
producing ethylene by converting a stream comprising an oxygenate into a first product stream comprising ethylene and ethane through an oxygenate-to-olefins process;
producing ethylene oxide by subjecting ethylene and ethane from the first product stream comprising ethylene and ethane to oxidation conditions resulting in a second product stream comprising ethylene oxide, unconverted ethylene and ethane;

recovering ethylene oxide from the second product stream comprising ethylene oxide, unconverted ethylene and ethane; and converting the ethylene oxide to monoethylene glycol through an hydrolysis reaction.

In the above ethane steam cracking embodiment of the present process, additional ethylene is produced by converting a stream comprising ethane into a stream comprising ethylene and unconverted ethane. In the present invention, it is also envisaged that additional ethylene is produced by converting a hydrocarbon stream comprising naphtha, gasoil or hydrowax into a stream comprising ethylene and ethane, similar to the above-mentioned ethane steam cracking embodiment.

That is to say, a preferred embodiment of the present process for the production of monoethylene glycol, comprising the steps of:

producing ethylene by converting a stream comprising an oxygenate into a first product stream comprising ethylene and ethane through an oxygenate-to-olefins process;

producing ethylene oxide by subjecting ethylene and ethane from the first product stream comprising ethylene and ethane to oxidation conditions resulting in a second product stream comprising ethylene oxide, unconverted ethylene and ethane;

recovering ethylene oxide from the second product stream comprising ethylene oxide, unconverted ethylene and ethane; and converting the ethylene oxide to monoethylene glycol through an hydrolysis reaction.

Preferably, in the above preferred embodiment, said hydrocarbon stream is a stream comprising ethane, naphtha, gasoil or hydrowax or any mixture thereof.

In the present specification, "naphtha" refers to a mixture comprising saturated hydrocarbons which have a boiling point ranging from 20 to 200° C. Generally, said hydrocarbons have between 5 and 12 carbon atoms. Further, "gasoil" refers to a mixture comprising saturated hydrocarbons which have a boiling point ranging from 200 to 600° C., and "hydrowax" refers to a mixture comprising saturated hydrocarbons which have a boiling point ranging from 250 to 700° C.

In the above steam cracking embodiments of the present process, the steam cracking process is carried out in a reactor different from the reactor used in converting the stream comprising an oxygenate into a stream comprising ethylene and ethane.

Further, in the above steam cracking embodiments of the present process, in general hydrogen is produced as a by-product. The hydrogen may be separated from the product streams using any suitable means known in the art, for example by cryogenic distillation, by pressure swing absorption whereby hydrogen absorbs preferentially, or via a hydrogen permeable membrane. The separated hydrogen may be used to produce methanol, from said hydrogen and carbon monoxide and/or carbon dioxide, which methanol can then be used as a feedstock for the ethylene production step comprising oxygenate conversion of the present invention.

In the above steam cracking embodiments of the present process, the ethylene oxidation step also results in a stream comprising ethylene oxide, unconverted ethylene and ethane. For example, in the ethane steam cracking embodiment of the present process, said "ethane" in the latter stream comprises both ethane by-product that originates from converting a stream comprising an oxygenate and unconverted ethane that originates from ethane steam cracking.

Also in the above steam cracking embodiments of the present process, as already discussed above in general, it is preferred that a stream comprising unconverted ethylene and ethane is separated from the stream comprising ethylene oxide, unconverted ethylene and ethane, that results from the ethylene oxidation step, and is recycled to the step of producing ethylene oxide.

In the above steam cracking embodiments of the present process, ethane from the stream comprising ethylene oxide, unconverted ethylene and ethane (unconverted ethane and/or by-product ethane) resulting from the step of producing ethylene oxide may be recycled to the steam cracking step of producing ethylene. Either part or all ethane is recycled in such way. This has the advantage that more ethylene may be produced by recycling ethane (unconverted ethane and/or by-product ethane) whereas ethane that is not converted after such recycle will then automatically be re-used as a ballast gas in the ethylene oxidation step. That is to say, also in those embodiments of the present invention where a hydrocarbon stream is cracked in an additional step, which stream is an ethane, naphtha, gasoil or hydrowax stream, such recycled ethane may be converted into ethylene.

Further, in the above steam cracking embodiments of the present process, ethane from the stream comprising ethylene oxide, unconverted ethylene and ethane (unconverted ethane and/or by-product ethane) resulting from the step of producing ethylene oxide may be recycled to both the step of producing ethylene oxide and to the steam cracking step of producing ethylene. Both types of recycle of ethane are illustrated in FIG. 2, as further discussed below, with reference to the ethane steam cracking embodiment.

Where in the present specification reference is made to recycling to the "step of producing ethylene" or "ethylene production step", or recycling to the "step of producing ethylene oxide", "ethylene oxide production step" or "ethylene oxidation step", such steps not only cover the step(s) of production of the desired product in question but also the step(s) of work-up of the product stream in question.

Preferably, in the above steam cracking embodiments of the present process, a stream comprising unconverted ethylene and ethane (unconverted ethane and/or by-product ethane) is separated from the stream comprising ethylene oxide, unconverted ethylene and ethane (unconverted ethane and/or by-product ethane) and is recycled to the step of producing ethylene oxide. Further, preferably, said separated stream comprising unconverted ethylene and ethane (unconverted ethane and/or by-product ethane) is further separated into a stream comprising unconverted ethylene which is recycled to the step of producing ethylene oxide and a stream comprising ethane (unconverted ethane and/or by-product ethane) which is recycled to the steam cracking step of producing ethylene. This is illustrated in FIG. 2, as further discussed below, with reference to the ethane steam cracking embodiment.

In addition, advantageously, the latter separation is not critical so that a complete separation of ethane from ethylene is not needed. In the above steam cracking embodiments of the present process, ethane is (ethane steam cracking embodiment) or can be (other steam cracking embodiments) starting material in the ethylene production step in question and is at the same time ballast gas in the subsequent ethylene oxide production step. All that matters is that the separated substream which comprises more ethylene than the other separated substream is recycled to the step of producing ethylene oxide, whereas the other separated substream is recycled to the ethylene production step in question.

In the flow scheme of FIG. 2, which illustrates the above ethane steam cracking embodiment of the present process, stream 1 comprising a feed containing an oxygenate is fed to ethylene production unit 2. Stream 3 comprising ethylene and ethane and stream 4 comprising an oxidizing agent, such as high-purity oxygen or air, are fed to ethylene oxide production unit 5. Stream 15 comprising a feed containing ethane is fed to ethylene production (steam cracker) unit 16. Stream 17 comprising ethylene and unconverted ethane is fed, via stream 3, to ethylene oxide production unit 5. Stream 6 comprising ethylene oxide, unconverted ethylene, ethane and carbon dioxide is sent to ethylene oxide separation unit 7. Ethylene oxide is recovered via stream 8. Further, stream 9 comprising unconverted ethylene, ethane and carbon dioxide is split into two substreams 9a and 9b. Substream 9a is recycled to ethylene oxide production unit 5. Substream 9b is fed to carbon dioxide removal unit 10. Stream 11 comprising unconverted ethylene and ethane is split into two substreams 11a and 11b. Substream 11a is recycled to ethylene oxide production unit 5. Substream 11b is fed to ethylene/ethane separation unit 12. Stream 13 comprising unconverted ethylene is recycled to ethylene oxide production unit 5. Stream 14 comprising ethane is recycled to ethylene production unit 16. Further, a third stream may be separated in ethylene/ethane separation unit 12, namely a top bleed stream comprising uncondensable components, such as oxygen and/or argon (said third stream not shown in FIG. 2). Still further, stream 3 may be subjected to hydrotreatment in a hydrotreater unit before entering ethylene oxide production unit 5 (said hydrotreater unit not shown in FIG. 2) to convert any acetylene present.

In the present invention, additional ballast gas, such as nitrogen or methane, may be added to the ethylene oxide production step. However, it is also envisaged in the above steam cracking embodiments of the present process that the conversion and/or selectivity in the ethylene production step in question (that is to say, the steam cracking step), is tuned depending on the desired amount of ballast gas needed in the ethylene oxide production step. That is to say, for example in said ethane steam cracking embodiment, in case the demand for ballast gas in the ethylene oxide production step is relatively low, conversion in said ethylene production step may be set higher such that relatively less unconverted ethane is present in the product stream resulting from said ethylene production step. And, conversely, in case the demand for ballast gas in the ethylene oxide production step is relatively high, conversion in said ethylene production step may be set lower such that relatively more unconverted ethane is present in the product stream resulting from said ethylene production step. Alternatively, conversion in said ethylene production step may be kept constant and additional ballast gas, such as nitrogen or methane, may be added to the ethylene oxide production step, as mentioned above. For example, the conversion in said ethylene production step may range from 5 to 90%, suitably from 10 to 60%.

Alternatively or additionally, the ethane from the stream comprising ethylene oxide, unconverted ethylene and ethane resulting from the step of producing ethylene oxide is not recycled or not completely recycled to the step of producing ethylene oxide and/or is not recycled or not completely recycled to the steam cracking step of producing ethylene, but is used as a fuel for providing heat, by combustion, to the various steps of the present process, including one or more of the ethylene production step comprising oxygenate conversion, the ethylene oxide production step and the optional ethylene production step comprising hydrocarbon steam cracking.

The above advantageous embodiment is exemplified in FIG. 2 as described above, with the proviso that in the latter embodiment stream 14 is not fed to ethylene production (steam cracker) unit 16, but is used as a fuel for providing heat, by combustion, for example to ethylene production unit 2, ethylene production unit 16 and/or ethylene oxide production unit 5.

In general, in steam cracking a hydrocarbon stream into ethylene, methane may be produced as a by-product. Separating any methane from the stream comprising ethylene and ethane is not essential in terms of obtaining the advantages of the present invention as described herein. It is even preferred that methane, if any, is not separated from the latter stream. In this way, methane may function as a ballast gas, in combination with ethane, in the ethylene oxidation step. This is advantageous first of all in that the methane does not have be separated, which is cumbersome, and secondly in that in a case where additional ballast gas needs to be added to the ethylene oxide production step, this may no longer be needed as the mixture of methane and ethane may provide a sufficient amount of ballast gas for the ethylene oxide production step.

In the above steam cracking embodiments of the present process, the cracking process is performed at elevated temperatures, preferably in the range of from 650 to 1000° C., more preferably of from 750 to 950° C. The conversion is typically in the range of from 40 to 75 mol %, based on the total number of moles of hydrocarbon provided to the cracking zone. Steam cracking processes are well known to the skilled person and need no further explanation. Reference is for instance made to Kniel et al., Ethylene, Keystone to the petrochemical industry, Marcel Dekker, Inc, New York, 1980, in particular chapter 6 and 7.

In the above steam cracking embodiments of the present process, it is preferred to combine at least part of the stream comprising ethylene and ethane obtained from the step of producing ethylene by the conversion of a stream comprising an oxygenate with at least part of the stream comprising ethylene and ethane obtained from the steam cracking step, that is to say the step of producing ethylene by converting a hydrocarbon stream (comprising ethane, naphtha, gasoil and/or hydrowax) into a stream comprising ethylene and ethane, prior to sending the streams to a work-up section. By combining at least part of these two streams, a more efficient use of the work-up facilities is achieved. In addition, by combining at least part of these two streams, also the smaller fractions in these streams may be more efficiently separated.

Preferably, at least part of the ethylene oxide is converted to monoethylene glycol (MEG), which is a useful liquid product. The conversion of ethylene oxide to MEG may be done using any MEG producing process that uses ethylene oxide. Typically the ethylene oxide is hydrolysed with water to MEG. Optionally, the ethylene oxide is first converted with carbon dioxide to ethylene carbonate, which is subsequently hydrolysed to MEG and carbon dioxide. The water is provided to the MEG zone as a feed containing water, preferably pure water or steam. The MEG product is obtained from the MEG zone as a MEG-comprising effluent. Suitable processes for the production of ethylene oxide and MEG are described for instance in US2008139853, US2009234144, US2004225138, US20044224841 and US2008182999, the disclosures of which are herein incorporated by reference. The invention is further illustrated by the following Example.

Example

In this experiment, ethylene was oxidized into ethylene oxide (EO) over a rhenium-containing catalyst prepared according to US20090281345 and having a silver content of 17.5 wt. %, using air as a source of oxygen (oxidizing agent), using ethane as ballast gas, and using ethyl chloride (EC) as moderator.

The experiment was performed in a "single-pass" or "once-through" mode without any recycle. An inlet gas stream was contacted with the catalyst in a U-shaped tubular steel microreactor that was immersed in a temperature-controlled molten metal bath. The inlet gas stream comprised 25 vol. % of ethylene, 8.3 vol. % of oxygen, 0.6 vol % of carbon dioxide, 260 parts per million by volume (ppmv) of EC, 32.3 vol. % of ethane, the balance comprising nitrogen originating from the air that was used as the source of oxygen and from the blend containing EC that was used as the moderator.

A gas flow rate of 254 cc/minute was directed through a 4.6 g charge of catalyst, providing a gas hourly space velocity (GHSV) of 2,850 $hr^{-1}$. Total pressure was 16.5 bar gauge. Generation of 3.48 vol. % EO in the product stream corresponded to a work rate of 195 kg of product per cubic meter of catalyst bed per hour ($kg/m^3/hr$). The catalyst temperature to achieve said target work rate was 244° C.

Results of the experiment are shown in Table 1 below. The experiment shows that ethane can be used as a ballast gas in the oxidation of ethylene to EO. In addition, when using ethane as ballast gas, the selectivity of the ethylene oxidation reaction to EO is high. Furthermore, ethane is converted to only a small extent.

TABLE 1

| | |
|---|---|
| Oxygen conversion | 46.6% |
| Ethylene conversion | 15.2% |
| Ethane conversion | 0.7% |
| Selectivity of conversion of ethylene to EO | 88.9% |

The invention claimed is:

1. A process for the production of monoethylene glycol, comprising the steps of:
   a. producing ethylene by converting a stream comprising an oxygenate into a first product stream comprising ethylene and ethane through an oxygenate-to-olefins process;
   b. producing ethylene oxide by subjecting ethylene and ethane from the first product stream comprising ethylene and ethane to oxidation conditions resulting in a second product stream comprising ethylene oxide, unconverted ethylene and ethane;
   c. recovering ethylene oxide from the second product stream comprising ethylene oxide, unconverted ethylene and ethane; and
   d. converting the ethylene oxide to monoethylene glycol through an hydrolysis reaction.

2. A process according to claim 1, wherein the ethylene oxide is first converted with carbon dioxide to ethylene carbonate which is then hydrolysed to monoethylene glycol and carbon dioxide.

3. A process according to claim 1, wherein a stream comprising unconverted ethylene and ethane is separated from the second product stream comprising ethylene oxide, unconverted ethylene and ethane and is recycled to the step of producing ethylene oxide.

4. A process according to claim 1, wherein the first product stream comprising ethylene and ethane further comprises methane.

5. A process according to claim 1, wherein the first product stream comprising ethylene and ethane further comprises acetylene and the first product stream comprising ethylene and ethane is subjected to hydrotreatment to convert any acetylene prior to subjecting ethylene and ethane from the first product stream comprising ethylene and ethane to oxidation conditions.

6. A process according to claim 4, wherein the first product stream comprising ethylene and ethane further comprises hydrogen and at least part of the hydrogen is used to convert at least part of the acetylene.

7. A process for the production of monoethylene glycol, comprising the steps of:
   a. producing ethylene by converting a stream comprising an oxygenate into a first product stream comprising ethylene and ethane through an oxygenate-to-olefins process;
   b. producing ethylene by converting a stream comprising ethane into a second product stream comprising ethylene and unconverted ethane through a steam cracking process;
   c. producing ethylene oxide by subjecting ethylene and ethane from the first product stream comprising ethylene and ethane and the second product stream comprising ethylene and unconverted ethane to oxidation conditions resulting in a stream comprising ethylene oxide, unconverted ethylene and ethane;
   d. recovering ethylene oxide from the stream comprising ethylene oxide, unconverted ethylene and ethane; and
   e. converting the ethylene oxide to monoethylene glycol through an hydrolysis reaction.

8. A process according to claim 7, wherein the ethylene oxide is first converted with carbon dioxide to ethylene carbonate which is then hydrolysed to monoethylene glycol and carbon dioxide.

9. A process according to claim 7, wherein ethane from the stream comprising ethylene oxide, unconverted ethylene and ethane is recycled to the step of producing ethylene which latter step comprises converting a stream comprising ethane into a stream comprising ethylene and unconverted ethane.

10. A process according to claim 7, wherein ethane from the stream comprising ethylene oxide, unconverted ethylene and ethane is recycled to the step of producing ethylene oxide and to the step of producing ethylene which latter step comprises converting a stream comprising ethane into a stream comprising ethylene and unconverted ethane.

11. A process according to claim 7, wherein a stream comprising unconverted ethylene and ethane is separated from the stream comprising ethylene oxide, unconverted ethylene and ethane, the stream comprising unconverted ethylene and ethane is separated into a stream comprising unconverted ethylene which is recycled to the step of producing ethylene oxide and a stream comprising ethane which is recycled to the step of producing ethylene which latter step comprises converting a stream comprising ethane into a stream comprising ethylene and unconverted ethane.

* * * * *